United States Patent [19]
Buchecker et al.

[11] Patent Number: 5,335,303
[45] Date of Patent: Aug. 2, 1994

[54] QUASI-PHASED MATCHED OPTICAL WAVEGUIDE FREQUENCY CONVERSION ELEMENT HAVING A FERROELECTRIC LIQUID CRYSTALLINE MATERIAL EXHIBITING A PERIODIC STRUCTURE

[75] Inventors: Richard Buchecker, Zurich, Switzerland; Xin H. Chen, Berlin, Fed. Rep. of Germany; Jürg Fünfschilling, Basel, Switzerland; Rolf-Peter Herr, Freiburg, Fed. Rep. of Germany; Martin Schadt, Seltisberg, Switzerland; Klaus Schmitt, Lörrach, Fed. Rep. of Germany

[73] Assignee: Hoffmann-La Roche Inc., Nutley, N.J.

[21] Appl. No.: 102,676

[22] Filed: Aug. 5, 1993

Related U.S. Application Data

[63] Continuation of Ser. No. 899,085, Jun. 15, 1992, abandoned.

[30] Foreign Application Priority Data

Jun. 25, 1991 [CH] Switzerland ............. 1878/91
Jan. 10, 1992 [CH] Switzerland ............. 65/92

[51] Int. Cl.$^5$ ............................. H03F 7/00
[52] U.S. Cl. ....................... 385/122; 3459/42; 3459/103; 3459/332; 385/143; 385/145
[58] Field of Search ............ 359/42, 326, 332, 93, 359/94, 95, 103; 385/122, 143, 145

[56] References Cited

U.S. PATENT DOCUMENTS

| | | | |
|---|---|---|---|
| 4,865,406 | 9/1989 | Khanarian et al. | 359/332 |
| 4,971,416 | 11/1990 | Khanarian et al. | 359/332 |
| 5,002,361 | 3/1991 | DeMartino et al. | 359/332 |
| 5,028,109 | 7/1991 | Lawandy | 359/332 |
| 5,044,725 | 9/1991 | DeMartino et al. | 385/141 |
| 5,064,265 | 11/1991 | Khamarian et al. | 359/332 |

FOREIGN PATENT DOCUMENTS

| | | |
|---|---|---|
| 301511 | 2/1989 | European Pat. Off. |
| 304738 | 3/1989 | European Pat. Off. |
| 368042 | 5/1990 | European Pat. Off. |

OTHER PUBLICATIONS

Derwent Abstract 89-062436/09 (Feb. 1989) for EP 304 738.
Kapitza, H. et al., Ferroelectric Liquid Crystalline Polysiloxanes with High Spontaneous Polarization and Possible Applications in Nonlinear Optics in *Advanced Materials 2*, No. 11, pp. 539-543, after Jul. 4, 1990.
J. Y. Liu et al., *Optics Let.*, 15(5), 267-269, (Mar. 1990).
A. N. Vtyurin et al., *Sov. Phys. Cryst.*, 26(3), pp. 309-310, (May-Jun. 1981).
A. Fukuda et al., *Jap. J. of Appl. Phys.*, 28, L997-L999, (1989) (no month available).
M. Ozaki et al., *Tech. Reports of Osaka Univ.*, 39 (1972), pp. 217-222, (Oct. 1989).
L. M. Blinov et al., *Liquid Crystals*, 2(2), pp. 121-130, (1987) (no month available).
M. I. Barnik et al., *Sov. Phys. JETP*, 59(5), pp. 980-981, (May 1984).
Tang et al., *IEEE J. Of Quantum Electr.*, QE-9(1), pp. 9-17, (Jan. 1973).
Levine et al., *Appl. Phys. Lett.*, 26(7), pp. 375-377, (Apr. 1975).
Feng et al., *Appl. Phys. Let.*, 37(7), pp. 607-609, (Oct. 1980).
S. Somekh et al., *Optics Communications*, 6(3), pp. 301-304, (Nov. 1972).
Clark et al., *Appl. Phys. Lett.*, 36(11), pp. 899-901 (Jun. 1980).
Funfschilling et al., *Japanese Journal Of applied Physics*, vol. 30(4) pp. 741-746 (Apr. 1991).

*Primary Examiner*—Frank Gonzalez
*Attorney, Agent, or Firm*—George M. Gould; George W. Johnston; Robert A. Silverman

[57] ABSTRACT

An optical frequency conversion element has a waveguiding layer which consists of a $\chi^{(2)}$-active ferroelectric liquid crystal. The monomeric or polymeric liquid crystal material has a periodic structure which permits the so-called quasi phase matching of a guided laser beam. The period length of the structure is equal to twice the coherence length $l_c = \pi/\Delta\beta$ of the material, whereby $\Delta\beta = \beta_o(2\omega) - 2\beta_o(\omega)$, with $\omega$ = angular frequency of the fundamental wave, 0 = zero-order mode and $\beta$ = propagation constant of the mode.

11 Claims, 1 Drawing Sheet

QUASI-PHASED MATCHED OPTICAL WAVEGUIDE FREQUENCY CONVERSION ELEMENT HAVING A FERROELECTRIC LIQUID CRYSTALLINE MATERIAL EXHIBITING A PERIODIC STRUCTURE

This is a continuation of application Ser. No. 07/899,085 filed Jun. 15, 1992 (now abandoned).

FIELD OF THE INVENTION

The invention relates to an optical element for efficient generation of short-wave laser light by frequency conversion using a wave-guiding layer, and compounds suitable for manufacturing this layer.

BACKGROUND OF THE INVENTION

In a large number of applications the present trend of development is to replace electronic or opto-mechanical components by electro-optical or pure optical components based on non-linear optical ("nlo") effects, because in principle these operate faster, more reliably and more economically than the former. Many of these applications, e.g. optical storage systems with high data density, would require compact rugged laser light sources emitting in the range of <500 nm. Since short-wave laser diodes are not available and have not hitherto been realizable, attempts have been made for a long time to convert long wave-length light from conventional laser diodes efficiently into short wave-length light by non-linear optical materials, particularly by frequency doubling ("Second Harmonic Generation: SHG"), summation of frequencies, etc. Techniques which permit the integration of the laser diode with the nlo active material in an integrated optical device would be particularly attractive.

Efficient frequency conversion can be obtained only if the "phase-matching" condition for the irradiated long wave-length light and the generated short wavelength light can be fulfilled in the nlo-active medium. This can be achieved with suitable non-linear crystals such as KDP, ADP, $LiNbO_3$, etc.

Since the efficiency of conversion depends on the square of the power density of the fundamental wave and since the light intensity of available laser diodes is relatively small, impracticably large and expensive nlo crystals are required. The conditions are much more favorable if the conversion can be made in waveguide configurations instead of in the aforementioned crystals. In wave guiding configurations, light is compressed to a small cross-section, thus increasing the power density by several orders of magnitude. In addition, the waveguide geometry makes it easier to fulfill the phase-matching condition. The following are three possible phase matching techniques:

First if the use of the dispersion property of various modes in the waveguide. If the waveguide is correctly dimensioned, the phase-matching condition is fulfilled for the fundamental wave when guided in low-order modes and for the second harmonic guided in a higher mode. However, the conversion efficiency depends on the square of the overlapping integral between the two modes and is small for modes of different order.

Second is the use of the birefringence of anisotropic waveguides. This method corresponds to the situation in birefringent crystals and is applicable only to materials with suitable birefringence. In this case, conversion between modes of the same order (e.g. TE→TM) is possible, so that large values of the overlapping integral can be obtained.

Third is the use of periodic structures. With this method, known as quasi phase-matching, the non-linearity of the waveguide material is periodically modulated. This method has become important recently, since it is relatively easy to carry out in poled structures (e.g. poled nlo polymers). In periodic structures conversion also occurs between modes of the same order (e.g. $TE_0(\omega) \rightarrow TE_0(2\omega)$) and is therefore highly efficient.

In the present state of the art, $\chi^{(2)}$-active materials potentially suitable for the aforementioned waveguides are the following classes:

1. Monocrystalline inorganic layers.
One typical example is $LiNbO_3$, which has been particularly intensively studied, inter alia because of its high non-linear coefficients $d_{31} = -5.95$ ppm/V and $d_{33} = -37$ pm/V, and is frequently used as a reference material for judging nlo substances. One disadvantage, however, is that $LiNbO_3$-layers are difficult to prepare and are very expensive.

2. $\chi^{(2)}$-active Langmuir-Blodgett multilayers. These have the disadvantage that they are unstable, particularly with respect to temperature.

3. Poled $\chi^{(2)}$-active polymers. Their disadvantage is the instability of their nlo-coefficients with time.

SUMMARY OF THE INVENTION

The object of the invention is to provide a novel frequency-converting optical element in which the wave-guiding layer is free from the aforementioned disadvantages.

This is achieved in accordance with the invention, which provides an optical element of the kind described above in which the wave-guiding layer consists of a ferroelectric $\chi^{(2)}$-active monomeric or polymeric liquid crystalline material having a periodic structure which permits quasi phase-matching of a guided laser beam, the period length of the three-dimensional structure being equal to twice the coherence length $l_c = \pi/\Delta\beta$ of the material, whereby $\Delta\beta = \beta_o(2\omega) - 2\beta_o(\omega)$, with $\omega$=angular frequency of the fundamental wave, 0 =zero-order mode and $\beta$=propagation constant of the mode.

The invention also relates to P-nitro-aniline derivates which can be used to manufacture the optical element. The compounds having the formula:

In this formula the following applies:

$X^1$, $X^2$: one of which denotes $-NO_2$ and the other denotes $-NR^5R^6$ in which $R^5$ and $R^6$ each independently is H or lower alkyl;

$R^3$, $R^4$: each independently denote H, F, Cl, Br, $NH_2$, $NO_2$, CN, lower alkyl or lower alkoxy, with the proviso that $X^1$ is different from $R^4$ and $X^2$ is different from $R^3$;

$R^1$: denotes chiral alkyl or cycloalkyl in which, independently of each another, one or two non-adjacent $-CH_2$ groups can be replaced by O, S, $-COO-$, $-OOC-$, $-HC=CH-$ and in an aliphatic residue also by —C≡C— and which can be mono- or poly-substituted by F, Cl, CN, lower alkyl or lower alkoxy, with the proviso that the center of chirality is situated in an alkyl chain on the first or second C atom and on a carbon atom in the case of a cycloalkyl residue;

$A^1$: denotes 1 to 4 six-membered rings which are bonded to one another or to the p-nitro-aniline ring by a single covalent bond and/or at one or optionally a number of sites via —CH$_2$—CH$_2$—, —CH$_2$O—, —OCH$_2$—, —COO—, —OOC—, —COS—, —SOC—, —CH=CH—, —C≡C—, —N=N—, —N=NO—, —ON=N—, —CH=N, —N=CH— or butylene, in which a —CH$_2$CH$_2$— group can be replaced by —COO—, —OOC—, —HC=CH— or —C≡C— and/or a —CH$_2$— group can be replaced by O or S. The six-membered rings in $A^1$, independently of one another, are 1,4-phenylene which is unsubstituted or optionally mono-, di- or polysubstituted with F, Cl, lower alkyl or lower alkoxy and in which one or two —CH— groups can be replaced by nitrogen, or 1,4-cyclohexylene in which one or two —CH$_2$— groups (preferably not adjacent) can be replaced by O or S or a —CH$_2$CH$_2$— group can be replaced by —CH=CH—, or naphthalene-2,5-diyl, decalin-2,6-diyl, tetralin-2,6-diyl, thiadiazolyl or oxodiazolyl;

$Z^1$: denotes a single covalent bond, —CH$_2$—CH$_2$—, —$_{CH2}$O—, —OCH$_2$—, —COO—, —OOC—, —COS—, —SOC—, —CH=CH—, —C≡C—, —N=N—, —N=NO—, —ON=N—, —CH=N, —N=CH— or butylene in which one —CH$_2$CH$_2$— group can be replaced by —COO—, —OOC—, —HC=CH— or —C≡C— and/or a —CH$_2$— group can be replaced by 0 or S;

$A^2$: denotes the structural element wherein $X^1$, $X^2$, $R^3$ and $R^4$ have the significance given previously;

n: denotes 0 or 1;

$R^2$: denotes chiral or achiral alkyl or cycloalkyl in which, independently of one another, one or more non-adjacent —CH$_2$— groups can be replaced by O, S, —COO—, or —HC=CH— and in an aliphatic residue also by —C≡C— or 1,4-phenylene and which can be mono- or poly-substituted by F, Cl, CN, lower alkyl or lower alkoxy, with the proviso that any center of chirality is situated in an alkyl chain on the first or second C atom and in the case of a cycloalkyl residue on a carbon atom in the ting, or, where n is the number 0, $R^2$ also denotes the group wherein $X^1$, $X^2$, $R^1$, $R^3$, $R^4$ and $A^1$ have the above significance and m is a whole number of 6-16 and wherein one or two non-adjacent —CH$_2$— groups, independently of one another, can be replaced by O, S, —COO—, —CH=CH— or —C≡C—.

DETAILED DESCRIPTION OF THE INVENTION

The invention relates to an optical element for efficient generation of short-wave laser light by frequency conversion by means of a wave-guiding layer. The wave-guiding layer consists of a ferroelectric $\chi^{(2)}$-active monomeric or polymeric liquid crystalline material having a periodic structure which permits a quasi phase matching of a guided laser beam. The period length of the three-dimensional structure being equal to twice the coherence length $l_c = \pi/\Delta\beta$ of the material, whereby $\Delta\beta = \beta_o(2\omega) - 2\beta_o(\omega)$, with $\omega$ = angular frequency of the fundamental wave, 0 = zero-order mode and $\beta$ = propagation constant of the mode.

In an alternative embodiment of the invention, the material, owing to its birefringent properties, can be used to phase match the $d_{21}$ components of the nlo tensor.

In another embodiment, the ferroelectric liquid crystal material forms an $S^*_c$ phase or a higher-ordered ferroelectric phase which can be dipolarly oriented in the electric field.

In another embodiment, the ferroelectric material forms an $S^*_c$ phase which is homogeneously oriented in a bistable manner by boundary forces. This occurs in the surface-stabilized ferroelectro (SSF) configuration with materials having a large helical pitch or with short pitch bistable ferroelectric (SBF) materials. The electro-optical properties of ferroelectric liquid crystals which are relevant for displays (LCDs) have been thoroughly investigated. Liquid crystals displays may, for example, be based on the "Surface Stabilized Ferroelectric effect" (SSF) [see Clark N. A. et al., Appl. Phys. Lett. 36 (1980), 899] and the "Short-Pitch Bistable Ferroelectric effect" (SBF) [see Fünfschilling J. et al., Jpn. J. Appl. Phys. 30(1991) 741].

Preferably, the ferroelectric liquid crystal material consists of a mixture of chiral nlo-active molecules which form $S^*_c$ phases.

Preferably, the dipolar orientation is fixed by cooling below the glass transition temperature.

In another embodiment, the optical element is operated as a Pockels device, i.e. as an electro-optical switch or light modulator in the spectral range from 1300 to 430 nm.

Preferably, the nlo-material has the phase sequence 1-Chol-Sm$_A$S$^*_c$-glass. Optionally, the element is operated in the $S^*_c$ phase, so that when an electric field is applied the $\chi^{(2)}$ property becomes operative but disappears when the electric field is switched off.

More particularly, the optical element can be used for doubling the frequency of laser light in the wavelength 850–1300 nm, preferably 900–1300 nm, and can be optically coupled to a laser diode emitting in the range from 850–1300 nm to form a frequency doubling module.

In another embodiment, the dipolarly oriented axis is at right angles to the waveguide plane.

Ferroelectric liquid crystals for use in second-order non-linear devices have the following very attractive properties. They combine the ease of preparation of devices which are based on poled nlo-polymers with the intrinsic non-centrosymmetric structure of $\chi^{(2)}$-active monocrystals.

In principle, both, low-molecular and polymeric ferroelectric liquid crystals are candidates for $\chi^{(2)}$-active materials, because in the ferroelectric phase, e.g. the chiral smectic C phase ($S^*_c$), they possess the non centro-symmetrical structure which is a prerequisite for nlo-activity. In the $S^*_c$ phase, under suitable conditions, these substances form a helical structure which can be converted to a planar dipolarly oriented structure e.g. by applying a weak electric field. In that case the oriented dipoles will be at right angles to the liquid crystal director. Such a structure exhibits a high degree of order, thus providing a high nlo-activity.

Thin $\chi^{(2)}$-active films of low-molecular ferroelectric liquid crystal mixtures have so far not been considered to be important or practical. This opinion results from discouraging previously published SHG data on ferroelectric liquid crystal mixtures. These exhibit non-linear coefficients which are so low (e.g. $d_{22}=0.027$ pm/V; $d_{23}=0.07$ pm/V; $d_{16}=0.0026$ pm/V, Ref. 4), they are of no industrial use whatsoever.

Ferroelectric liquid crystal mixtures consist either of chiral mesogenic molecules forming $S^*_c$ phases or a combination of mesogenic molecules forming $S_c$ phases and chiral dopants capable of inducing the $S^*_c$ phase.

It has been found that efficient $\chi^{(2)}$-active ferroelectric liquid crystal materials can be achieved by incorporating nlo-active structural elements having a high second-order hyperpolarizability in the aforementioned chiral substances, such that the axis which is relevant for the non-linearity becomes dipolarly oriented in the ferroelectric liquid crystal configuration.

As is known, molecules having the form A Π D, where A is and electron acceptor, Π denotes a bridge with a delocalized electron system and D denotes an electron donor, are hyperpolarizable along the donor-acceptor axis. Paranitroaniline is an example of a molecule of this kind.

Mesogenic molecules forming ferroelectric liquid crystal phases are rod-shaped (length>>width). Consequently nlo-active molecular groups incorporated transversely to the director must be compact. Otherwise they will destroy the liquid crystalline phase. The same applies to the chiral nlo dopants. This requirement limits the attainable hyperpolarizability.

Also, there is a direct relation between the value of the non-linearity and the short wave-length limit of the transparent spectral region of the nlo molecule. To obtain frequency conversion into the blue spectral region, the material must be transparent in this region.

5-Amino-2-nitro-1,4-phenylene has proven to be excellent as an nlo-active structural element. Surprisingly, it has been found that if this nlo structural element is suitably incorporated in a properly designed smectogenic molecule, an $S^*_c$ phase results.

It has also been found that the axis relevant for the non-linearity of the nlo group can be given a highly ordered dipolar orientation in the $S^*_c$ phase if the nlo unit is incorporated close to the chiral group of the liquid crystal molecule or the chiral dopant molecule.

From SHG measurements (1064 nm-532 nm conversion) follow values of the order of 10 pm/V and 5 pm/V, respectively, for the non-linear coefficients $d_{22}$ and $d_{21}$ of these materials. These values are hundred times larger than the largest previously published data and are comparably large as those for $LiNbO_3$. These high non-linear coefficients correspond to the observed high values of the spontaneous polarization (up to 700 $nC/cm^2$). Analysis of the measurements shows a near-perfect dipolar orientation of the molecules in the smectic layers. A new class of molecules with the previously described properties has been found. The new superior nlo properties of the new compounds are a consequence of their molecular design concept which is described in the following.

The substances are p-nitro-aniline derivatives having the formula:

I

In this formula the following applies:
$X^1$, $X^2$: one of which denotes —$NO_2$ and the other denotes —$NR_5R^6$ in which $R^5$ and $R^6$ each independently is H or lower alkyl;
$R^3$, $R^4$: each independently denote H, F, Cl, Br, $NH_2$, $NO_2$, CN, lower alkyl or lower alkoxy, with the proviso that $X^1$ is different from $R^4$ and $X^2$ is different from $R^3$;
$R^1$: denotes chiral alkyl or cycloalkyl in which, independently of each another, one or two non-adjacent —$CH_2$ groups can be replaced by O, S, —COO—, —OOC—, —HC=CH— and in an aliphatic residue also by —C≡C— and which can be mono- or poly-substituted by F, Cl, CN, lower alkyl or lower alkoxy, with the proviso that the center of chirality is situated in an alkyl chain on the first or second C atom and on a carbon atom in the case of a cycloalkyl residue;
$A^1$: denotes 1 to 4 six-membered rings which are bonded to one another or to the p-nitro-aniline ring by a single covalent bond and/or at one or optionally a number of sites via —$CH_2$—$CH_2$—, —$CH_2O$—, —$OCH_2$—, —COO—, —OOC—, —COS—, —SOC—, —CH=CH—, —C≡C—, —N=N—, —N=NO—, —ON=N—, —CH=N, —N=CH— or butylene, in which a —$CH_2CH_2$— group can be replaced by —COO—, —OOC—, —HC=CH— or —C≡C— and/or a —$CH_2$— group can be replaced by O or S. The six-membered tings in $A^1$, independently of one another, are 1,4-phenylene which is unsubstituted or optionally mono-, di- or polysubstituted with F, Cl, lower alkyl or lower alkoxy and in which one or two —CH— groups can be replaced by nitrogen, or 1,4-cyclohexylene in which one or two —$CH_2$— groups (preferably not adjacent) can be replaced by O or S or a —CH$_2$CH$_2$— group can be replaced by —CH=CH—, or naphthalene-2,5-diyl, decalin-2,6-diyl, tetralin-2,6-diyl, thiadiazolyl or oxodiazolyl;

Z$^1$: denotes a single covalent bond, —CH$_2$—CH$_2$—, —CH$_2$O—, —OCH$_2$—, —COO—, —OOC—, —COS—, —SOC—, —CH=CH—, —C≡C—, —N=N—, —N=NO—, —ON=N—, —CH=N—, —N=CH— or butylene in which one —CH$_2$CH$_2$— group can be replaced by —COO—, —OOC—, —HC=CH— or —C≡C— and/or a —CH$_2$— group can be replaced by O or S;

A$^2$ denotes the structural element wherein X$^1$, X$^2$, R$^3$ and R$^4$ have the significance given previously;

n: denotes 0 or 1;

R$^2$: denotes chiral or achiral alkyl or cycloalkyl in which, independently of one another, one or more non-adjacent —CH$_2$— groups can be replaced by O, S, —COO—, or —HC=CH— and in an aliphatic residue also by —C≡C— or 1,4-phenylene and which can be mono- or poly-substituted by F, Cl, CN, lower alkyl or lower alkoxy, with the proviso that any center of chirality is situated in an alkyl chain on the first or second C atom and in the case of a cycloalkyl residue on a carbon atom in the ting, or, where n is the number 0, R$^2$also denotes the group wherein X$^1$, X$^2$, R$^1$, R$^3$, R$^4$ and A$^1$ have the above significance and m is a whole number of 6-16 and wherein one or two non-adjacent —CH$_2$— groups, independently of one another, can be replaced by O, S, —COO—, —CH=CH— or —C≡C—.

Preferred compounds of formula I are those in which R$^2$ can be chiral or achiral alkyl or cycloalkyl in which, independently of one another, one or two non-adjacent —CH$_2$— groups can be replaced by 0, S, —COO—, —HC=CH— and in an aliphatic residue also by —C≡C— and which can be mono- or multiply- substituted by F, Cl, CN, lower alkyl or lower alkoxy, with the proviso that any center of chirality is situated in an alkyl chain on the first or second C atom and in the case of a cycloalkyl residue on a carbon atom in the ring, or, where n is the number 0, R$^2$ also can be the group wherein X$^1$, X$^2$, R$^1$, R$^3$, R$^4$ and A$^1$ have the above significance and m is a whole number of 6-16 and wherein one or two non-adjacent —CH$_2$— groups, independently of one another, can be replaced by O, S, —COO—, —CH=CH— or —C≡C—.

In the compounds of formula I above the residues R$^1$ and R$^4$and/or (where n=1) R$^2$ and R$^3$ or R$^2$ and R$^4$ can be interchanged, if desired.

The term "chiral or achiral alkyl or cycloalkyl in which, independently or one another, one or more non-adjacent —CH$_2$— groups can be replaced by O, S, —COO— or —HC=CH— and in an aliphatic residue also by —C≡C— or 1,4-phenylene and which can be mono- or poly-substituted by F, Cl, CN, lower alkyl or lower alkoxy" embraces in the scope of this invention straight-chain or branched residues with 1 to 16, preferably 4 to 12, carbon atoms such as alkyl, alkoxy, alkoxyalkyl, alkenyl, alkenyloxy, alkenyloxyalkyl, alkoxycarbonyl, alkoxycarbonylalkoxy, alkanoyloxy, 1-haloalkyl, 2-haloalkyl, 2-haloalkoxy, 2-haloalkoxycarbonyl, 1-cyanoalkyl, 2-cyanoalkyl, 2-cyanoalkoxy, 2-cyanoalkoxycarbonyl, 1-methylalkyl, 2-methylalkyl, 2-methylalkoxy, 2-methylalkoxycarbonyl, 1-methoxyalkyl, 2-methoxyalkyl, 2-methoxyalkoxy, 2-methoxyalkoxycarbonyl, 8-acryloyloxyoctanoxy, 9-acryloyloxynonanoxy, 10-acryloyloxydecanoxy, 11-acryloyloxyundecanoxy, 12-acryloyloxydodecanoxy, 8-methacryloyloxyoctanoxy, 9-methacryloyloxynonanoxy, 10-methacryloyloxydecanoxy, 11-methacryloyloxyundecanoxy, 12-methacryloyloxydodecanoxy, 8-(2-chloroacryloyloxy)octanoxy, 9-(2-chloroacryloyloxy)-nonanoxy, 10-(2-chloroacryloyloxy)decanoxy, 11-(2-chloroacryloyloxy)-undecanoxy, 12-(2-chloroacryloyloxy)-dodecanoxy, 8-vinyloxyoctanoxy, 9-vinyloxynonanoxy, 10-vinyloxydecanoxy, 8-vinyloxycarbonyloctanoxy, 9-vinyloxycarbonylnonanoxy, 10-vinyloxycarbonyldecanoxy, 11-vinyloxycarbonyldecanoxy, 12-vinyloxycarbonyldodecanoxy, 8-(4-styryl)oxyoctanoxy, 9-(4-styryl)oxynonanoxy, 10-(4-styryl)oxydecanoxy, 11-(4-styryl)oxyundecanoxy, 12-(4-styryl)oxydodecanoxy, 8-(4-styryl)methylenoxyoetanoxy, 9-(4-styryl)methyleneoxynonanoxy, 10(4-styryl)methyleneoxydecanoxy, 11-(4-styryl)methyleneoxyundecanoxy, 12-(4-styryl)methyleneoxydodecanoxy, 7-octenyloxy, 8-nonenyloxy, 9-decenyloxy, 10-undecenyloxy, 11-dodecenyloxy and the like, as well as 4 to 7-membered saturated, optionally chiral rings such as cyclopentyl, cyclohexyl, 2-oxiranyl, 2-tetrahydropuran, 2-tetrahydropyranyl, 2-methylcyclohexyl, 2-methylcyclopentyl or the like.

The terms "lower alkyl" and "lower alkoxy" denote in the scope of the invention straight-chain alkyl and, respectively, alkoxy groups with 1 to 4 carbon atoms, such as methyl, ethyl, propyl, butyl, methoxy, ethoxy, propyloxy or butyloxy, particularly methyl, ethyl or methoxy or ethoxy.

The term "1,4-phenylene which is unsubstituted or substituted by F, Cl, lower alkyl and/or lower alkoxy and in which 1 or 2 CH groups is/are optionally re- placed by nitrogen" embraces groups such as 1,4-phenylene, 2-fluoro-1,4-phenylene, 2,3-difluoro-1,4-phenylene, 2-chloro-1,4-phenylene. 2-methyl-1,4-phenylene, pyridine-2,5-diyl, pyrazine-2,5-diyl, pyrimidine-2,5-diyl, pyridazine-3,6-diyl and the like. Preferred groups are 1,4-phenylene, 2-fluoro-1,4-phenylene, 2,3-difluoro-1,4-phenylene, pyridine-2,5-diyl, pyrazine-2,5-diyl, pyrimidine-2,5-diyl and the like.

The term "1,4-cyclohexylene in which one or two non-neighbouring —$CH_2$— groups can be replaced by 0 or S or one —$CH_2CH_2$— group can be replaced by —CH=CH—" includes trans-1,4-cyclohexylene, 1,3-dioxane-2,5-diyl, 1,3-dithiane-2,5-diyl and the like.

The term "tetralin-2,6-diyl" denotes 1,2,3,4-tetrahydro-naphthalene-2,6-diyl. The term "trans-decalin-2,6-diyl" embraces 2,6-disubstituted groups derived from trans-decahydronaphthalene, more particularly (4a$\alpha$H,-8a$\beta$H)-decahydronaphthalene-2$\alpha$,6$\beta$-diyl and the like.

The non-linear optical compounds of the invention all have a multi-substituted p-nitroanilino group which combines with known liquid-crystal structural units to give the previously described excellent properties to this class of compounds. p-nitro-anilines with a suitable substitution pattern are available commercially or can be prepared in a manner known per se. These preparative methods are also described in the following Schemes 1 and 2 and in Examples 1 to 5.

Scheme 1

-continued
Scheme 1

DCC = N,N'-Dicyclocarbodiimide
DMAP = 4-(Dimethylamino)pyridine

Scheme 2

-continued
Scheme 2

In these Schemes the individual substituents have the significance given earlier.

Formula I includes molecules which themselves form S*$_c$ phases and can therefore be used as such as $\chi^{(2)}$-active waveguide material.

A second group is formed by molecules which do not themselves form S*$_c$ phases, but which, as chiral dopants, induce S*$_c$ phases in suitable S$_c$ matrix mixtures.

Further, compounds of formula I can also be used as monomers for the formation of LC-side chain polymers which have a ferroelectric phase. For this purpose there are preferably used compounds of the formula Ia wherein $X^1$, $X^2$, $R^3$, $R^4$, $R^1$ and $A^1$ each have the significance given above and $R^5$ is chiral or achiral alkyl in which, independently of one another, one or more —CH$_2$— groups can be replaced by —O—, —S—, —COO—, —HC=CH— or 1,4-phenylene and which can be mono- or poly-substituted with F, Cl, CN, lower alkyl and lower alkoxy.

Especially preferred compounds for the formation of polymeric $\chi^{(2)}$ active materials are compounds of formula Ia in which $R^5$ carries in the terminal position for example one of the following polymerizable groups:

Accordingly, LC-side chain polymers, which can be manufactured, for example, by polymerizing acrylic acid derivatives, styryl derivatives and the like or by polymer-like reactions of alkenes with poly(methyl hydrogen siloxanes), also form an object of the invention.

Surprisingly, among these nlo-active ferroelectric liquid crystal substances and mixtures of substances, examples have been found which change into the glass state at low temperatures and in the process freeze the dipolar order induced in the S*$_c$ phase at a higher temperature. Clearly, these forms of low-molecular nlo-active ferroelectric liquid crystal glass are particularly attractive for industrial use, since the nlo properties are preserved after oriented freezing of the material.

The LC-side chain polymers manufactured from compounds of formula I, especially of formula Ia, generally have the properties corresponding to the monomers; that is to say, they have a ferroelectric S$_C$* phase and non-linear optical properties.

Another application of the proposed substances and polymers is through use of the bistability in surface stabilized ferroelectric (SSF) configurations. As is known, ferroelectric liquid crystals with a sufficiently large helical pitch assume bistable switching states in suitably prepared cells. The required large helical pitch can be realized by compensation in ferroelectric liquid crystal mixtures. In this case a dipolar ordered homogeneous orientation, which is advantageous for efficient generation of frequency conversion, can be adopted through action of a short electric pulse. An electric pulse of opposite polarity switches the film back into the non-phase-matched orientation.

The same use can be made of the recently discovered surface bistable ferroelectric (SBF) configuration, except that a small helical pitch is required in this case. This condition is fulfilled by many of the aforementioned nlo substances.

Non-bistable configurations, e.g. of the "deformed helix ferroelectric" (DHF) type [see Beresnev L. A. et al., Liquid Crystals 5 (1989), 1171] can also be considered for use according to the invention as $\chi^{(2)}$-active layers. In this case, by applying a relatively low voltage the material can be given a dipolar orientation and thus made $\chi^{(2)}$-active. This orientation is retained only as long as the field is applied. After the voltage has been switched off, the layer relaxes into a $\chi^{(2)}$-inactive state.

It will be clear to a person skilled in the art that the previously described possible uses of the $S^*_c$ phase also apply to the higher-order ferroelectric phases (I*, F*, G*, H*, J*, K*).

Embodiments of the optical element according to the invention will now be described with reference to the accompanying drawings.

Figure 1:
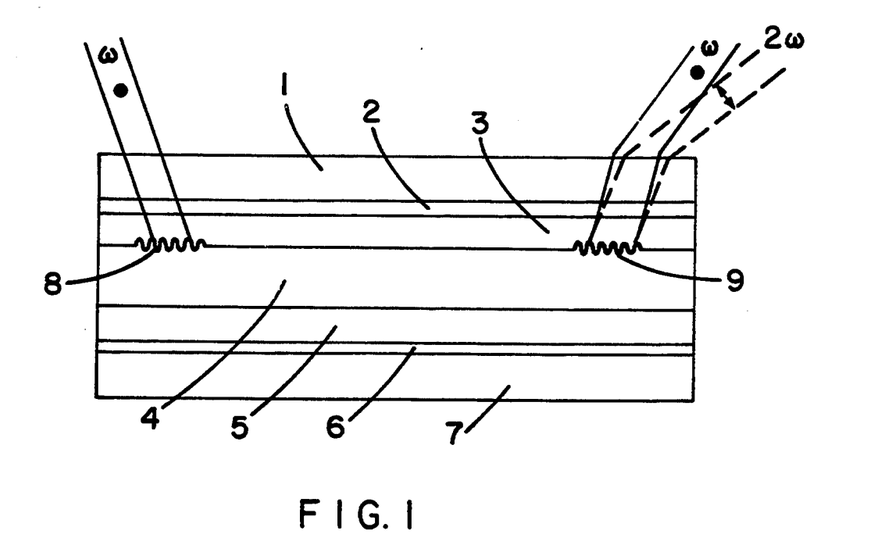
FIG. 1 is a diagrammatic section through a waveguide element.

FIG. 1 shows an optically non-linear waveguide element having the structure of a liquid crystal cell and comprising two glass plates 1, 7 coated with transparent electrodes 2, 6. Polymeric surface-treated cladding layers 3, 5 with a low refractive index are disposed on the electrode layers. A ferroelectric liquid crystal 4 is disposed between the two thus-coated plates. The thickness of the liquid crystal is fixed by a spacer (not shown). The cladding layers homogeneously orient the liquid crystal layer and are also used for guiding the optical waves in the liquid crystal. An optical grating 8 for coupling light into the liquid crystal layer 4 and an optical grating 9 for coupling light out are embossed in the cladding layer 3.

During manufacture, the space between the coated plates is filled with a ferroelectric liquid crystal mixture and homogeneously oriented in the electric field. In the ferroelectric phase, a d.c. field is applied and aligns the lateral dipoles of the ferroelectric liquid crystal molecules at right angles to the plane of the plate. The mixture is cooled below the glass temperature while the d.c. field is applied, so that the dipolarly oriented layer is frozen in a glassy state.

Light from a laser diode emitting in the red or IR region is coupled into the waveguide element via one of the grating embossed in the cladding layer, so that the light propagates as an extraordinary beam in a mode of TE-character. If the layer thickness and the direction of propagation are correctly chosen relative to the direction of the director, an effective propagation constant $\beta(\omega)$ of the TE mode can be adjusted at a value such that the second harmonic generated via the non-linear coefficient $d_{21}$ travels through the layer with phase matching and is in the form of a TM-like wave. At the end of the cell, the fundamental and the frequency-doubled wave are coupled out via the second optical grating embossed in the cladding layer.

As an alternative to coupling in via a grating, as described here, the methods of prism and face coupling as known from the literature may be used.

Figure 2:
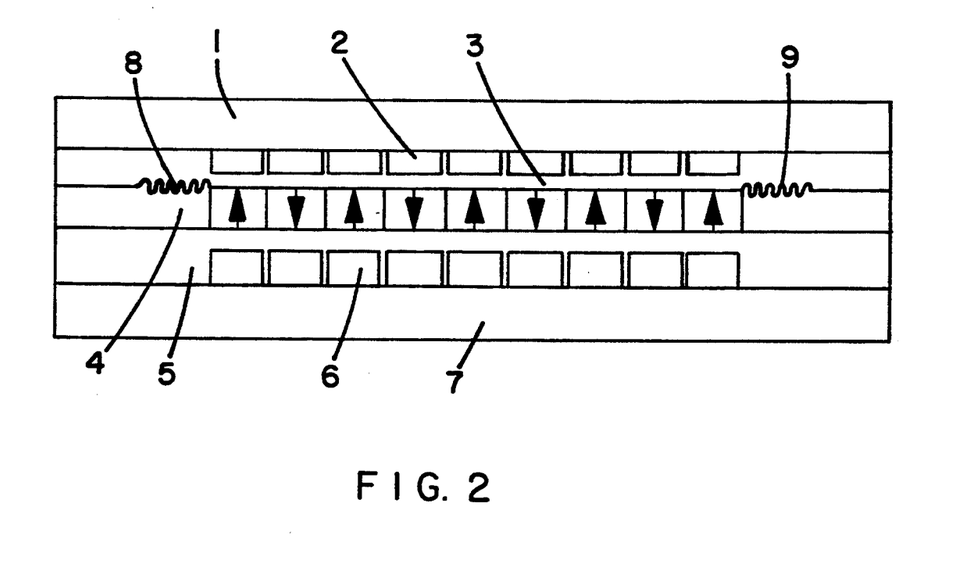
FIG. 2 is a diagrammatic section through an alternative waveguide configuration.

FIG. 2 shows an optical waveguide element comprising a liquid crystal layer with a periodically poled structure. As in FIG. 1, it comprises two glass plates 1, 7 coated with transparent electrodes 2, 6. However, the electrodes have a grating structure used for spatially alternate poling of the liquid crystal layer. Polymeric surface-treated cladding layers 3, 5 with a low index of refraction are disposed above the electrode layers. A ferroelectric liquid crystal 4 is disposed between the coated plates. Optical gratings 8, 9 for coupling light into and out of the liquid crystal layer 4 are embossed into the cladding layer 3.

The period has the length $2l_c = 2\pi/\Delta\beta$ with $\Delta\beta = \beta(2\omega) - 2\beta(\omega)$ and $\omega$ denotes the angular frequency of the fundamental wave and $\beta$ is the propagation constant.

This quasi phase-matching method enables the maximum nlo coefficient $d_{22}$ to be used. Light is coupled in by the methods described in connection with FIG. 1.

The invention will be illustrated in more detail by the following Examples. In each case the optical antipodes of chiral compounds have the same phase transition temperatures and the same absolute twist values, but with opposite sign.

The abbreviations used for characterizing the phase transitions have the following meanings:
C stands for crystalline;
S stands for smectic;
$S_A$, $S_B$, $S_C$ etc stands for smectic A, B, C etc;
$S^*_c S^*_F$ etc stands for chiral smectic C, F etc;
N stands for nematic;
Ch stands for cholesteric;
I stands for isotropic

EXAMPLE 1

5-Amino-2-nitro-4-[(R)-2-octyloxy]benzoic acid (0.06 g), 0.1 g of 4-(5-heptyl-2-pyrimidinyl)phenol and 0.04 g of 4-(dimethylamino)pyridine were dissolved in 10 ml of dichloromethane and the solution was treated portionwise within 10 minutes with 0.07 g of N,N'-dicyclohexylcarbodiimide while stirring. The mixture was stirred at room temperature for 40 hours, filtered and concentrated. Chromatography of the residue on silica gel with ethyl acetate/dichloromethane (vol. 1:8) and recrystallization from diethyl ether/hexane (vol. 1:1), gave 0.09 g of 4-(5-heptyl-2-pyrimidinyl)phenyl 5-amino-2-nitro-4-[(R)-2-octyloxy]benzoate of melting point 105° C.

The 5-amino-2-nitro-4-[(R)-2-octyloxy]benzoic acid used as the starting material was prepared as follows:

a) A solution of 10 g of 4-hydroxy-3-nitrobenzoic acid and 370 ml of ethyl alcohol was prepared and then hydrogen chloride gas was introduced for 5 hours. The reaction mixture was poured on to 1300 ml of ice-water and the separated solid was filtered off, washed with 50% ethyl alcohol and dried. This gave 8.5 g of ethyl 4-hydroxy-3-nitrobenzoate of melting point 68.5°–69.5° C. as yellow crystals.

b) A mixture of 4 g of ethyl 4-hydroxy-3-nitrobenzoate, 5.4 g of (S)-2-octyl benzenesulphonate 6.9 g of potassium carbonate and 110 ml of ethyl methyl ketone was heated to reflux overnight. Subsequently, the cooled reaction mixture was poured into water and extracted three times with 50 ml of diethyl ether each time. The combined organic phases were washed with 500 ml of water, dried over magnesium sulphate, filtered and concentrated. Chromatography of the residue on silica gel with dichloromethane gave 5.6 g of ethyl 3-nitro-4-[(R)-2-octyloxy)benzoate as of a yellow oil.

c) A mixture of 1.7 g of ethyl 3-nitro-4-[(R)-2-octyloxy]benzoate and 50 ml of ethyl alcohol was hydrogenated over 0.1 g of platinum(II) oxide until the uptake of hydrogen had finished. The catalyst was filtered off and the filtrate was concentrated. Chromatography of the residue on silica gel with dichloromethane gave 1.5 g of ethyl 3-amino-4-[(R)-2-octyloxy]benzoate as a colourless oil.

d) A solution of 0.5 g of ethyl 3-amino-4-[(R)-2-octyloxy]benzoate, 3.4 ml of methanol, 1.7 ml of water and 0.4 g of potassium hydroxide was heated to reflux for 4 hours. Most of the methanol was then distilled off and the reaction mixture was first treated with 50 ml of water and then made slightly acid with concentrated sulphuric acid. The separated solid was filtered off and dried. This gave 0.44 g of 3-amino-4-[(R)-2-octyloxy]-benzoic acid with $[\alpha]_D^{20} = -29.3°$.

e) A solution of 1 g of 3-amino-4-[(R)-2-octyloxy]benzoic acid and 12 ml of acetic anhydride was heated at 90° C. for 1 hour and then treated with 100 ml of water. The solid formed was separated from the cooled reaction mixture and dried. This gave 0.9 g of 3-acetylamino-4-[(R)-2-octyloxy]benzoic acid.

f) A solution of 0.4 ml of nitric acid and 0.3 ml of acetic acid was treated portionwise with 0.1 g of 3-acetylamino-4-[(R)-2-octyloxy]benzoic at 0° C., stirred at this temperature for 10 minutes and then at 20° C. for 10 minutes and then poured on to 6 g of ice-water. The separated solid was filtered off and then dissolved in concentrated potassium carbonate solution. The solution was extracted twice with 50 ml of ethyl acetate each time. The combined organic phases were washed twice with 50 ml of water each time, dried over sodium sulphate, filtered and then concentrated. This gave 5-acetylamino-2-nitro-4-[(R)-2-octyloxy]benzoic acid which was used in the next step without further purification.

The following compounds can be prepared in similar manner:

4-(Nonyloxy)-4'-biphenylyl] 5-amino-2-nitro-4-[(R)-2-octyloxy)benzoate, m.p. (C-I) 140°–142° C.;
4'-[4-(trans-4-pentylcyclohexyl)butyl]-4-biphenyl 5-amino-2-nitro-4-[(R)-2-octyloxylbenzoate;
p-(trans-5-decyl-m-dioxan-2-yl)phenyl 5-amino-2-nitro-4-[(R)-2-octyloxy]benzoate;
p-(trans-5-[(E)-1-heptenyl]-m-dioxan-2-yl)phenyl 5-amino-2-nitro-4-[(R)-2-octyloxy]benzoate;
p-(trans-5-[(E)-1-heptenyl]-m-dioxan-2-yl)phenyl 5-amino-4-[(R)-2-fluorohexanoyloxyl]-2-nitrobenzoate;
p-(trans-5-[(E)-1-heptenyl]-m-dioxan-2-yl)phenyl 5-amino-4-[(2S,3S)-2-fluoro-3-methylvaleroyloxy]-2-nitrobenzoate;
p-(trans-5-[(E)-1-heptenyl]-m-dioxan-2-yl)phenyl 5-amino-4-[(S)-2-methylbutyloxy]-2-nitrobenzoate;
4-[5-(trans-5-heptyl-m-dioxan-2-yl)pyridin-2-yl]phenyl 5-amino-4-[(R)-2-fluorohexanoyloxyl]-2-nitrobenzoate;
5-(p-octylphenyl)-2-pyrazinyl 5-amino-2-nitro-4-[(R)-2-octyloxy]benzoate;
5-[p-(trans-4-pentylcyclohexyl)phenyl]-2-pyrazinyl 5-amino-4-[(S)-2-methylbutyloxy]-2-nitrobenzoate;
4-[2-(p-octylphenyl)ethynyl]phenyl 5-amino-2-nitro-4-[(R)-2-octyloxy]benzoate;
4-[2-(p-octylphenyl)ethynylphenyl 5-amino-4-[5-hexenoxy-(R)-propionyl-2-oxy]-2-nitrobenzoate;
4'-(7-octenoxy)-4-biphenyl 5-amino-4-[7-octenoxy-(R)-propionyl-2-oxy]-2-nitrobenzoate;
p-[3-trans-4-pentylcyclohexy)propoxy]phenyl 5-amino-4-[oct-7-enoxy-(R)-propionyl-2-oxy]-2-nitrobenzoate;
p-[3-(trans-4-[pentylcyclohexyl)propoxy]phenyl 5-amino-4-[oct-3-enoxy-(R)-propionyl-2-oxy-2-nitrobenzoate.

EXAMPLE 2

A mixture of 5-dimethylamino-2-nitro-4-[(R)-2-octyloxy]-benzoic acid, 4-(5-heptyl-2-pyrimidinyl)-phenol, N,N'-dicyclohexylcarbodiimide, 4-(dimethylamino)pyridine and dichloromethane was reacted in an analogous manner to Example 1. This gave 4-(5-heptyl-2-pyrimidinyl)phenyl 5-dimethylamino-2-nitro-4-[(R)-2-octyloxy)benzoate as yellow crystals of melting point 60°–62° C. and $[\alpha]_D^{20} = +3°$.

The 5-dimethylamino-2-nitro-4-[(R)-2-octyloxy]benzoic acid used as the starting material was prepared as follows:

a) The esterification of 5-amino-2-nitro-2-[(R)-2-octyloxy]benzoic acid was carried out analogously to the synthesis of 4-(5-heptyl-2-pyrimidinyl)phenyl 5-amino-2-nitro-4-[(R)-octyloxy]benzoate. This gave ethyl 5-amino-2-nitro-4-[(R)-2-octyloxy]benzoate.

b) A mixture of 0.05 g of ethyl 5-amino-2-nitro-4-[(R)-2-octyloxy]benzoate, 0.13 g of sodium hydrogen carbonate, 2.5 ml of ethyl alcohol and 0.5 ml of methyl iodide was heated to reflux for 72 hours. The reaction mixture was filtered and then concentrated. Chromatography of the residue on silica gel with dichloromethane gave ethyl 5-dimethylamino-2-nitro-4-[(R)-2-octyloxy]benzoate which was used in the next step without further purification.

c) The saponification of ethyl 5-dimethylamino-2-nitro-4-[(R)-2-octyloxy]benzoate was carried out analogously to the synthesis of 3-amino-4-[(R)-2-octyloxy]-benzoic acid. This gave 5-dimethylamino-2-nitro-4-[(R)-2-octyloxy]benzoic acid.

The following compounds can be prepared in similar manner:

4'-[4-(trans-4-Pentylcyclohexyl)butyl]-4-biphenyl 4-[(R)-2-fluorohexanoyloxy]-5-dimethylamino-2-nitrobenzoate;
4'-[4-(trans-4-pentylcyclohexyl)butyl]-4-biphenyl 5-dimethylamino-4-[(R)-2-fluorohexanoyloxy]-2-nitrobenzoate.

EXAMPLE 3

2-Amino-5-nitro-4-[(R)-2-octyloxy]benzoic acid, 4-(6-heptyl-2-pyrimidinyl)phenol, N,N'-dicyclohexylcarbodiimide, 4-(dimethylamino)pyridine and dichloromethane were reacted in an analogous manner to Example 1. This gave 4-(5-heptyl-2-pyrimidinyl)phenyl 2-amino-5-nitro-4-[(R)-2-octyloxy]benzoate of melting point 105° C. and $[\alpha]_D^{20} = +19°$.

The 2-amino-5-nitro-4-[(R)-2-octyloxy]benzoic acid used as the starting material was prepared as follows:

a) A solution of 20 g of 4-toluidine and 400 g of concentrated sulphuric acid (d=1.84) was treated dropwise at 0° C. with a solution of 15 g of nitric acid (d=1.48) and sulphuric acid (d=1.84). The reaction temperature remained below 0° C. After completion of the addition the reaction mixture was stirred at 0° C. for a further hour and then poured on to 1200 ml of ice-water in such a manner that the reaction temperature did not rise above 25° C. The reaction mixture was further diluted with 4000 ml of water and then neutralized with sodium carbonate solution. The separated solid was filtered off, washed portionwise with water, dried and then recrystallized from ethyl alcohol. This gave 23 g of 4-methyl-3-nitroaniline as yellow crystals.

b) A solution of 10 g of 4-methyl-3-nitroaniline and 40 ml of acetic anhydride was heated to reflux for 15 minutes. The cooled reaction mixture was treated with 200 ml of water, cooled to 0° C. and then stirred at 0° C. for 30 minutes. The separated solid was filtered off and dried. This gave 11 g of 4-acetylamino-2-nitrotoluene.

c) A suspension of 10 g of 4-acetylamino-2-nitrotoluene, 8 g of magnesium sulphate and 500 g of water was heated to reflux and then treated portionwise with 24 g of potassium permanganate and 8 g of magnesium sulphate within 20 minutes. The reaction mixture was heated to reflux for 1.5 hours and then filtered while hot in order to remove residues of educt. The cooled reaction mixture was made slightly acid and the separated solid was filtered off and dried. This gave 5.6 g of 4-acetylamino-2-nitrobenzoic acid of melting point 217°-220° C.

d) The saponification of 4-acetylamino-2-nitrobenzoic acid was carried out analogously to the synthesis of 5-amino-2-nitro-4-[(R)-2-octyloxy]benzoic acid. This gave 4-amino-2-nitrobenzoic acid of melting point 244°-245° C.

e) A warm solution of 3 g of 4-amino-2-nitrobenzoic acid, 5 ml of water and 3.6 ml of concentrated sulphuric acid was cooled to 0° C., treated firstly with 8.5 g of ice-water and then with a solution of 1.3 g of sodium nitrite and 2.8 ml of water at 0° C. within 10 minutes. The reaction mixture was stirred at this temperature for 1 hour, then treated with 1.8 g of urea and filtered. The filtrate was added dropwise during 10 minutes to a boiling solution of 12 ml of concentrated sulphuric acid and 8.3 ml of water. The reaction o mixture was heated to reflux for 3 hours and then cooled to room temperature. The separated solid was filtered off. This gave 1 g 4-hydroxy-2-nitrobenzoic acid as yellow crystals of melting point 230° C. (decomposition).

f) The esterification of 4-hydroxy-2-nitrobenzoic acid was carried out in analogously to the synthesis of ethyl 4-hydroxy-3-nitrobenzoate. This gave ethyl 4-hydroxy-2-nitrobenzoate.

g) The esterification of 4-hydroxy-2-nitrobenzoic acid was carried out analogously to the synthesis of ethyl 3-nitro-4-[(R)-2-octyloxy]benzoate. This gave ethyl 2-nitro-4-[(R)-2-octyloxy]benzoate with $[\alpha]_D^{20} = -9.4°$.

h) The hydrogenation of ethyl 2-nitro-4-[(R)-nitrobenzoate was carried out analogously to the synthesis of ethyl 3-amino-4-[(R)-2-octyloxy]benzoate. This gave ethyl 2-amino-4-[(R)-2-octyloxy]benzoate as a colourless oil.

i) The saponification of ethyl 2-amino-4-[(R)-2-octyloxy]benzoate was carried out analogously to the synthesis of 3-amino-4-[(R)-2-octyloxy]benzoic acid. This gave 2-amino-4-[(R)-2-octyloxy]benzoic acid of melting point 94°-95.5° C.

j) The acylation of 2-amino-4-[(R)-2-octyloxy]benzoic acid was carried out analogously to the synthesis of 3-acetylamino-4-[(R)-2-octyloxy]benzoic acid with $[\alpha]_D^{20} = -4.4°$.

k) The nitration of 2-acetylamino-4-[(R)-2-octyloxy]benzoic acid was carried out analogously to the synthesis of 5-acetylamino-2-nitro-4-[(R)-2-octyloxy]benzoic acid. This gave 2-acetylamino-5-nitro-4-[(R)-2-octyloxy]benzoic acid.

l) The saponification of 2-acetylamino-5-nitro-4-[(R)-2-octyloxy]benzoic acid was carried out analogously to the synthesis of 5-amino-2-nitro-4-[(R)-2-octyloxy]benzoic acid. This gave 2-amino-5-nitro-4-[(R)-2-octyloxy]benzoic acid.

The following compounds can be prepared in an analogous manner:

4-(Nonyloxy)-4'-biphenylyl 2-amino-5-nitro-4-[(R)-2-octyloxy]benzoate, melting point 133°-134° C.;

4-[5-trans-5-heptyl-m-dioxan-2-yl)pyridin-2-yl]phenyl 2-amino-4-[(R)-2-fluorohexanoylozy]-5-nitrobenzoate;

4'-(dec-9-enyloxy)-4-biphenylyl 2-amino-5-nitro-4-[octyloxy(R)-propionyl-2-oxy]benzoate p-(5-heptyl-2-pyrimidinyl)phenyl 2-amino-4-[(S)-2-methylbutyloxy]-5-nitrobenzoate;

p-heptyloxyphenyl 2-amino-5-nitro-4-[(R)-2-octyloxy]benzoate;

4'-pentyl-4-biphenylyl 2-amino-5-nitro-4-[(R)-2-octyloxy]benzoate;

p-(trans-5-decyl-m-dioxan-2-yl)phenyl 2-amino-5-nitro-4-[(R)-2-octyloxy]benzoate;

p-[2-(trans-4-pentylcyclohexyl)ethyl]phenyl 2-amino-5-nitro-4-(R)-2-octyloxy]benzoate;

p-[2-(trans-4-pentylcyclohexyl)ethyl]phenyl 2-amino-4-[(2S,3S)-2-fluoro-3-methylvaleroyloxy]-5-nitrobenzoate;

4'-[4-(trans-4-pentylcyclohexyl)butyl-4-biphenylyl 2-amino-4[-(R)-2-fluorohexanoyloxy]-5-nitrobenzoate;

4'-[4-(trans-4-pentylcyclohexyl)butyl]-4-biphenyl 2-amino-5-nitro-4-[(R)-2-octyloxy]benzoate;

p-[3-(trans-4-pentylcyclohexyl)propoxyl]phenyl 2-amino-4-[(R)-2-fluorohexanoyloxy]-5-nitrobenzoate;

p-[3-(trans-4-pentylcyclohexyl)methoxy]phenyl 2-amino-4-[(R)-2-fluorohexanoyloxy]-5-nitrobenzoate;

4-[5-(trans-5-heptyl-m-dioxan-2-yl)pyridin-2-yl]phenyl 2-amino-4-[(R)-2-fluorohexanoyloxy]-5-nitrobenzoate;

p-(trans-5-[(E)-1-heptenyl-m-dioxan-2-yl)phenyl 2-amino-4-[(R)-2-fluorohexanoyloxy]-5-nitrobenzoate;

4'-(trans-5-[(E)-1-heptenyl-m-dioxan-2-yl)-4-biphenylyl 2-amino-4-[(R)-2-fluorohexanoyloxy]-5-nitrobenzoate;

5-[p-(heptyloxy)phenyl]-2-pyrazinyl 2-amino-5-nitro-4-[(R)-2-octyloxy]benzoate;

5-[p-(10-undecenyloxy)phenyl]-2-pyrazinyl 2-amino-4-[(R)-2-fluorohexanoyloxy]-5-nitrobenzoate;

5-[p-(trans-4-pentylcyclohexyl)phenyl]-2-pyrazinyl 2-amino-5-4[(R)-2-octyloxy]benzoate 5-[p-(trans-4-pentylcyclohexyl)phenyl]-2-pyrazinyl 2-amino-4-[(2S,3S)-2-fluoro-3-methylvaleroyloxy]-5-nitrobenzoate;

5-[p-[(R)-2-octyloxy]phenyl]-2-pyrazinyl 2-amino-5-nitro-4-[(R)-2-octyloxy]benzoat p-[(E)-4-octylstyryl]phenyl 2-amino-5-nitro-4-[(R)-2-octyloxy]benzoate;

4-[2-(p-octylphenyl)ethynyl]phenyl 2-amino-5-nitro-4-[(R)-2-octyloxy]benzoate;

4'-(10-undecenoxy)-4-biphenylyl 2-dimethylamino-4-[(R)-2-fluorohexanoyloxy]-5-nitrobenzoate;

4'-[(S)-3-methylpentyl]-4-biphenylyl 2-dimethylamino-4-[(2S,3S)-2-fluoro-3-methylvaleroyloxy]-5-nitrobenzoate;

hydroquinone bis[2-amino-5-nitro-4-[(R)-2-octyloxy]benzoate];

biphenyl 4,4'-bis[2-amino-5-nitro-4-[(R)-2-octyloxy]benzoate;

biphenyl 4,4'-bis[2-amino-4-[(R)-2-fluorohexanoyloxy]-5-nitrobenzoate.

EXAMPLE 4

The esterification of 4-[2-amino-5-nitro-4-[(R)-octyloxy]phenyl]benzoate with 4-hydroxy-4'-nonyloxybiphenyl was carried out analogously to the synthesis of 4'-(5-heptyl-2-pyrimidinyl)phenyl 5-amino-2-nitro-4-[(R)-2-octyloxy]benzoate. This gave 4'-(4-nonyloxyphenyl)phenyl 4-[2-amino-5-nitro-4-[(R)-2-octyloxy]phenyl]benzoate. M.p. (C-I) 90.1° C., transition ($S_C$-$S_A$) 132° C., transition ($S_A$-Ch) 186° C., point (Ch-I) clearing 190.6° C.

The 4-[2-amino-5-nitro-4-[(R)-2-octyloxy]phenyl]benzoic acid used as the starting material was prepared as follows:

a) A gaseous mixture of carbon dioxide and bromine was introduced into 10.5 g of molten m-nitrophenol heated in 120°–140° C. until the calculated increase in weight had been reached. Pure carbon dioxide was introduced to remove residues of bromine from the reaction mixture. The product mixture was recrystallized twice for 10% aqueous hydrochloric acid. This gave 8 g of 4-bromo-3-nitrophenol.

b) The etherification of 4-bromo-3-nitrophenol was carried out analogously to the synthesis of ethyl 3-nitro-4-[(R)-2-octyloxy]benzoate. This gave 1-bromo-2-nitro-4-[(R)-2-octyloxy]benzene.

c) A solution of 25.4 g of 2-(p-bromophenyl)-4,4-dimethyl-2-oxazoline in 100 ml of absolute tetrahydrofuran was added dropwise under nitrogen to 2.7 g of magnesium shavings so that the mixture boiled slightly as a result of the reaction. After completion of the addition the mixture was heated under reflux for a further 2 hours. The conversion was 95% (by gas chromatography).

20 ml of the solution of the Grignard reagent were added dropwise at −70° C. under a nitrogen atmosphere and with vigorous stirring to a mixture of 10 ml of triisopropyl borate and 0.5 ml of dry tetrahydrofuran. After completion of the addition the reaction mixture was warmed slowly to room temperature and stirred for a further 30 minutes. The reaction mixture was then poured into 100 ml of 10% hydrochloric acid. The solution was adjusted to pH 9 with solid sodium carbonate and extracted three times with 100 ml of ethyl acetate. The combined organic phases were washed twice with 100 ml of water, dried over sodium sulphate, filtered and concentrated. Chromatography of the residue on silica gel with a mixture of ethyl acetate and ethanol (vol. 2:1) gave a 4-[2-(4,4-dimethyl-2-oxazolyl)]phenylboric acid.

d) 0.6 g of 4-[2-(4,4-dimethyl-2-oxazolyl)]phenylboric acid in 1.14 ml of methanol and 2.88 ml of 2M aqueous sodium carbonate solution were added to a mixture of 0.684 g of 1-bromo-2-nitro-4-[(R)-2-octyloxy]benzene, 80 mg of Pd(PPh$_3$)$_4$ and 4.6 ml of toluene. The reaction mixture was heated to 80° C. for 48 hours with vigorous stirring. After cooling, 10 ml of 2M aqueous Na$_2$CO$_3$ solution and 1 ml of concentrated ammonia/water were added and the reaction mixture was extracted with 20 ml of methylene chloride. The organic phase was separated, dried over magnesium sulphate and concentrated. Chromatography of the residue on silica gel with a mixture of ethyl acetate and cyclohexane (vol. 2:3) finally gave 0.79 g of 2-[2'-nitro-4'-[(R)-2-octyloxy]-4-biphenylyl]-4,4-dimethyl-2-oxazoline.

e) 0.62 g of 2-[2'-nitro-4'-[(R)-2-octyloxy]-4-biphenylyl]-4,4-dimethyl-2-oxazoline was heated to 95° C. while stirring in 15 ml of 3N hydrochloric acid. After cooling, the precipitate was filtered off and washed with 10 ml of water. The precipitate was then heated to 70° C. for 40 minutes with vigorous stirring in 15 ml of 20% sodium hydroxide solution in methanol and water (vol. 1:1). After cooling, the reaction mixture was neutralized with concentrated hydrochloric acid. The precipitated solid was filtered off. After drying in a vacuum this gave 0.48 g of 4-[4'-[(R)-2-octyloxy]-2'-nitrophenyl]benzoic acid.

f) The reduction of 4-[4'-[(R)-2-octyloxy]-2'-nitrophenyl]benzoic acid was carried out analogously to the synthesis of ethyl 3-amino-4-[(R)-2-octyloxy]benzoate. This gave 4-[2-amino-4-[(R)-2-octyloxy]phenyl]benzoic acid.

g) The acetylation of 4-[2-amino-4-[(R)-2-octyloxy]phenyl]benzoic acid was carried out analogously to the synthesis of 3-acetylamino-4-[(R)-2-octyloxy]benzoic acid. This gave 4-[2-acetylamino-4-(R)-2-octyloxy]phenyl]benzoic acid.

h) The nitration of 4-[2-acetylamino-4-(R)-2-octyloxy]phenyl]benzoic acid was carried out analogously to the synthesis of 5-acetylamino-2-nitro-4-[(R)-2-octyloxy]benzoic acid. This gave 4-[2-acetylamino-5-nitro-4-[(R)-2-octyloxy]phenyl]benzoic acid.

i) The saponification of the amide function of 4-[2-acetylamino-5-nitro-4-[(R)-2-octyloxy]phenyl]benzoic acid was carried out analogously to the synthesis of 5-amino-2-nitro-4-[(R)-2-octyloxy]]benzoic acid. This gave 4-[2-amino-5-nitro-4-[(R)-2-octyloxy]phenyl]benzoic acid.

The following compounds can be prepared in an analogous manner:

4'-(5-Heptyl-2-pyrimidinyl)phenyl 4-[2-amino-5-nitro-4-[(R)-2-octyloxy]phenyl]benzoate. M.p. (C-I) 175°–176.1° C.

4'-(4-Heptyloxyphenyl 4-[2-amino-5-nitro-4-[(R)-2-octyloxy]phenyl]benzoate. M.p. (C-I) 95°–96.1° C., transition: ($S_A$-I) 74° C.

4'-(4-Pentylphenyl)phenyl 4-[2-amino-5-nitro-4-[(R)-2-octyloxy]phenyl]benzoate. M.p. (C-$S_A$) 142° C., transition ($S_A$-Ch) 160.8° C., transition (Ch-I) 168.1° C.

4-(2-trans-4-Pentylcyclohexy)ethyl]phenyl 4-[2-amino-5-nitro-4-[(R)-2-octyloxy]phenyl]benzoate. M.p. (C-$S_A$), transition ($S_A$-Ch) 132+ C., transition (Ch-I) 139° C., monotropic transition, ($S^*_C$-$S_A$) 62° C.

1,4-Phenylene bis[4-[2-amino-5-nitro-4-[(R)-2-octyloxy]phenyl]benzoate. M.p. (C-$S_A$) 175°, transition ($S_A$-Ch) 186° C., transition (Ch-I) 201° C.

EXAMPLE 5

The esterification of 4-[5-amino-2-nitro-4-[(R)-2-octyloxy]phenyl]benzoic acid with 4-hydroxy-4'-octyloxybiphenyl was carried out analogously to 4'-(5-hepty-2-pyrimidinyl)phenyl 5-amino-2nitro-4-[(R)-2-octyloxy]benzoate. This yielded 4'-(octyloxy)4-biphenylyl-4-[5-amino-2-nitro-4-[(R)-2-octyloxy]benzoate. M.p. (C-I) 177.8°–180.5° C., transition ($S_A$-Ch) 128° C., clearing point (Ch-I) 150° C.

The 4-[5-amino-2-nitro-4-[(R)-2-octyloxy]phenyl]benzoic acid used as the starting material was prepared as follows:

a) 4-(4-Hydroxyphenyl)benzoic acid was esterified with ethanol analogously to the synthesis of ethyl 4-hydroxy-3-nitro-benzoate. This gave ethyl 4-(4-hydroxyphenyl)benzoate.

b) The etherification of ethyl 4-(4-hydrophenyl)benzoate was carried out analogously to the synthesis of ethyl 3-nitro-4-[(R)-2-octyloxyl]benzoate. This gave ethyl 4-[4-[(R)-2-octyloxyl]phenyl]benzoate.

c) The saponification of ethyl 4-[4-(R)-2-octyloxy]phenyl]benzoate was carried out analogously to the synthesis of 3-amino-4-[(R)-2-octyloxy]benzoic acid. This gave 4-[4-(R)-2-octyloxy]phenyl]benzoic acid.

d) 3 g of 4-[4-(R)-octyloxy]phenyl]benzoic acid were dissolved in 110 ml of glacial acetic acid at 95° C. A mixture of 9 ml of fuming nitric acid and 9 ml of glacial acetic acid was added dropwise to the solution. The reaction mixture was heated while stirring to 90°–95° C. for a further hour and then heated to boiling for 10 minutes. Thereby, about 40 ml acetic acid were distilled off. The reaction mixture, cooled to room temperature, was poured on to 250 ml of ice-water and the resulting solid was filtered off. Recrystallization from 50% ethyl alcohol gave 2.6 g of 4-[3-nitro-4-[(R)-2-octyloxy]phenyl]benzoic acid.

e) The reduction of 4-[3-nitro-4-[(R)-2-octyloxy]phenyl]benzoic acid was carried out analogously to the synthesis of ethyl 3-amino-4-[(R)-2-octyloxy]benzoate. This gave 4-[3-amino-4-[(R)-2-octyloxy]phenyl]benzoic acid.

f) The acetylation of the amino group of 4-[3-amino-4-[(R)-2-octyloxy]phenyl]benzoic acid was carried out analogously to the synthesis of 3-acetylamino-4-[(R)-2-0octyloxy]benzoic acid. This gave 4-[3-acetylamino-4-[(R)-2-octyloxy]phenyl]benzoic acid.

g) 220 mg of 4-[3-acetylamino-4-[(R)-2-octyloxy]phenyl]benzoic acid were added in several portions to 2.8 ml of a mixture of nitric acid/glacial acetic acid (vol. 2:5) cooled with ice. After completion of the addition the reaction mixture was stirred at 0° C. for a further 20 minutes and then poured on to 100 ml of ice-water. The precipitated solid was filtered off and washed with water. The resulting 4-[5-acetylamino-2-nitro-4-[(R)-2-octyloxy]phenyl]benzoic acid was used without further purification in the subsequent reaction.

h) The saponification of the acetylamino group of 4-[5-acetylamino-2-nitro-4-[(R)-2-octyloxy]phenyl]benzoic acid was carried out analogously to the synthesis of 5-amino-2-nitro-4-[(R)-2-octyloxy]benzoic acid. This gave 160 mg of 4-[5-amino-2-nitro-4[(R)-2-octyloxy]phenylbenzoic acid.

The following compounds can be prepared in an analogous manner:

4'-[2-(trans-4-pentylcyclohexyl)ethyl]phenyl 4-[5-amino-2-nitro-4-[(R)-2-octyloxy]phenyl]benzoate. M.p. (C-I) 166.5°–167.6° C.

4'-(4-Pentyphenyl)phenyl 4-[5-amino-2-nitro-4-[(R)-2-octyl]phenyl]benzoate. M.p. (C-I) 187.2°–188.3° C.

4'-Heptyloxyphenyl 4-[5-amino-2-nitro-4-[(R)-2-octyl]phenyl]benzoate. M.p. (C-I) 136.5°–138.9° C.

EXAMPLE 6

Manufacture of poly{4-(11-acryloyloxyundecanoxy)phenyl 4-[2-amino-5-nitro-4-[(R)-2-octyloxy]phenyl]benzoate}: A solution of 1 g of 4-(11-acryloyloxyundecanoxy)phenyl 4-[2-amino-5-nitro 4-[(R)-2-octyloxy]phenyl]benzoate and 2.4 mg of α,α'-azoisobutyronitrile in 2.8 ml of toluene is gassed with argon at 0° C. for 10 min. and subsequently heated at 70° C. in a closed vessel for 48 hours. After cooling the polymerization mixture to room temperature the separated polymer is filtered off and dissolved in 10 ml of tetrahydrofuran. The solution is slowly added dropwise to 300 ml of methanol, whereby the polymer preciptates. This dissolution/precipitation procedure is repeated a further four times, the filtrate is dried in a vacuum and gives 0.57 g of poly{4-(11-acryloyloxyundecanoxy)phenyl 4-[2-amino-5-nitro-4-[(R)-2-octyloxy]phenyl]benzoate }. Glass transition: 55° C., transition ($S_C^*$-$S_A$): 109° C., transition ($S_A$-I): 128° C.

The monomeric 4-(11-acryloyloxyundecanoxy)phenyl 4-[2-amino-5-nitro-4-[(R)-2-octyloxy]phenyl]benzoate used as the starting material was prepared as follows:

a) 4-(11-Hydroxyundecanoxy)phenol: A mixture of 5 g of 11-bromundecanol and 5 g of hydroquinone in 200 ml of 2-butanone as well as 4 g of potassium carbonate is heated under reflux for 48 hours. The reaction mixture is filtered and the solvent is distilled off. The residue, dissolved in 400 ml of ethyl acetate, is washed four times with 100ml of a 10% (w/v) aqueous potassium carbonate solution each time and subsequently twice with water. The solution is dried over sodium sulphate, filtered and evaporated. Recrystallization from a small amount of ethyl acetate gives 4 g of 4-(11-hydroxyundecanoxy)phenol. M.p.: 99°–100.5° C.

b) 4-(11-Acryloyloxyundecanoxy)phenol: 5 g of 4-(11-hydroxyundecanoxy)phenol, 12 g of acrylic acid and 0.85 g of p-toluenesulphonic acid are dissolved in 250 ml of chloroform. The reaction mixture is heated under reflux on a water separator for 48 hours. After cooling the reaction mixture is washed twice with 100 ml of a 10% (w/v) sodium hydrogen carbonate solution each time and subsequently three times with 100 ml of water each time. After drying the organic phase over sodium sulphate the chloroform is distilled off and this gives 5.2 g of 4-(11-acryloyloxyundecanoxy)phenol. M.p. 72°–74° C.

c) 4-(11-Acryloyloxyundecanoxy)phenyl 4-[2-amino-5-nitro-4-[(R)-2-octyloxy]phenyl]benzoate: The esterification of 4-[2-amino-5-nitro-4-[(R)-2-octyloxy]phenyl]benzoic acid with 4-(11-acryloyloxyundecanoxy)phenol was carried out analogously to the synthesis of 4'-(5-heptyl-2-pyrimidinyl)phenyl [5-amino-2-nitro-4-[(R)-2-octyloxy]phenyl]benzoate (Example 3). This gave 2.6 g of 4-(11-acryloyloxyundecanoxy)phenyl 4-[2-amino-5-nitro-4-[(R)-2-octyloxy]phenyl]benzoate. Transition (KI-KII) 56.5°–58° C., m.p. (KIN) 68° C.

The following monomers can be prepared in an analogous manner:

4-(11-Acryloyloxyundecanoxy)phenyl 4-[2-amino-5-nitro-4-[(R)-2-octyloxy]phenyl]benzoat 4-(11-methacryloyloxyundecanoxy)phenyl 4-[2-amino-5-nitro-4-[(R)-2-octyloxy]phenyl]benzoate, 4-[11-(2-chloroacryloyloxy)undecanoxy]phenyl 4-[2-amino-5-nitro-4-[(R)-2-fluorohexanoyloxy]phenyl]benzoate, 4-(11-vinyloxyundecanoxy)phenyl 4-[2-amino-5-nitro-4-[(R)-2-octyloxy]phenyl]benzoate, poly{4-(10-vinyloxycarbonyldecanoxy)phenyl 4-[2-amino-5-nitro-4-[(R)-2-octyloxylphenyl]benzoate}, 4-[11-(4-styryl)oxyundecanoxy]phenyl 4-[2-amino-5-nitro-4-[(R)-2-octyloxy]phenyl]benzoate, 4-[11-(4-styryl)oxyundecanoxy]phenyl 4-[5-amino-4-[(2S,3S)-2-fluoro-3-methylvaleroyloxy]-2-nitrophenyl]benzoate,
4-[11-(4-styryl)methyleneoxyundecanoxy]phenyl 4-[2-amino-5-nitro-4-[(R)-2-octyloxy]phenyl]benzoate,
4-(10-undecenyloxy)phenyl 4-[2-N,N-dimethylamino-5-nitro-4-[(R)-2-octyloxy]phenyl]benzoate,
4-(11-acryloyloxyundecanoxy)phenyl 4-[5-amino-2-nitro-4-[(R)-2-octyloxy]phenyl]benzoate.

The following polymers can be manufactured therefrom in an analogous manner:

poly{4-(11-Acryloyloxyundecanoxy)phenyl 4-[2-amino-5-nitro-4-[(R)-2-octyloxy]phenyl]benzoate},
poly{4-(11-methacryloyloxyundecanoxy)phenyl 4-[2-amino-5-nitro-4-[(R)-2-octyloxy]phenyl]benzoate},
poly{4-[11-(2-chloroacryloyloxy)undecanoxy]phenyl 4-[2-amino-5-nitro-4-[(R)-2-fluorohexanoyloxy]-phenyl]benzoate},
poly{4-(11-vinyloxyundecanoxy)phenyl 4-[2-amino-5-nitro-4-[(R)-2-octyloxy]phenyl]benzoate},
poly{4-(10-vinyloxycarbonyldecanoxy)phenyl 4-[2-amino-5-nitro-4-[(R)-2-octyloxy]phenyl]benzoate},
poly{4-[11-(4-styryl)oxyundecanoxy]phenyl 4-[2-amino-5-nitro-4-[(R)-2-octyloxy]phenyl]benzoate},
poly{4-[11-(4-styryl)oxyundecanoxy]phenyl 4-[5-amino-4-[(2S,3S)-2-fluoro-3-methylvaleroyloxy]-2-nitrophenyl]benzoate},
poly{4-[11-(4-styryl)methyleneoxyundecanoxy]phenyl 4-[2-amino-5-nitro-4-[(R)-2-octyloxy]phenyl]benzoate},
poly{methyl [p-undecyloxyphenyl 4-[2-N,N-dimethylamino-5-nitro-4-[(R)-2-octyloxy]phenyl]benzoate]siloxane},
poly{4-(11-acryloyloxyundecanoxy)phenyl 4-[5-amino-2-nitro-4-[(R)-2-octyloxy]phenyl]benzoate}.

EXAMPLE 7

Manufacture of poly{4'-(11-acryloyloxyundecanoxy)-4-biphenylyl 4-[2-amino-5-nitro-4-[(R)-2-octyloxy]phenyl]benzoate}: The polymerization of 4'-(11-acryloyloxyundecanoxy)-4-biphenylyl 4-[2-amino-5-nitro-4-[(R)-2-octyloxy]phenyl]benzoate} was carried out analogously to the polymerization of 4-(11-acryloyloxyundecanoxy)phenyl 4-[2-amino-5-nitro-4-[(R)-2-octyloxy]phenyl]benzoate}. This gave 0.63 g of poly{4'-(11-acryloyloxyundecanoxy)-4-biphenylyl 4-[2-amino-5-nitro-4-[(R)-2-octyloxy]phenyl]benzoate}. Glass transition: 90° C., transition ($S_C^*$-$S_A$): about 140° C., transition ($S_A$-T): 270° C.

The monomeric 4'-(11-acryloyloxyundecanoxy)-4-biphenylyl 4-[2-amino-5-nitro-4-[(R)-2-octyloxy]phenyl]benzoate used as the starting material was prepared as follows:

a) 4-Hydroxy-4'-(11-hydroxyundecanoxy)biphenyl: The synthesis of 4-hydroxy-4'-(11-hydroxyundecanoxy)biphenyl was carried out analogously to the synthesis of 4-(11-hydroxyundecanoxy)phenol (Example 6a). This gave 4-hydroxy-4'-(11-hydroxyundecanoxy)biphenyl. M.p.: 144°–146° C.

b) 4'-(11-Acryloyloxyundecanoxy)-4-hydroxybiphenyl: The esterification of 4-hydroxy-4'-(11-hydroxyundecanoxy)biphenyl was carried out analogously to the esterification of 4-(11-hydroxyundecanoxy)phenol (Example 6b). This gave 4'-(11-acryloyloxyundecanoxy)-4-hydroxybiphenyl. M.p.: 91°–92° C.

c) 4'-(11-Acryloyloxyundecanoxy)-4-biphenylyl 4-[2-amino-5-nitro-4-[(R)-2-octyloxy]phenyl]benzoate: The esterification of 4'-(11-acryloyloxyundecanoxy)-4-hydroxybiphenyl with 4-[2-amino-5-nitro-4-[(R)-2-octyloxy]phenyl]benzoic acid was carried out analogously to the synthesis of 4-(11-acryloyloxyundecanoxy)phenyl 4-[2-amino-5-nitro-4-[(R)-2-octyloxy]phenyl]benzoate (Example 6c). This gave 4'-(11-acryloyloxyundecanoxy)-4-biphenylyl 4-[2-amino-5-nitro-4-[(R)-2-octyloxy]phenyl]benzoate, m.p.: 110° C., transition ($S_A$-I): 137° C., monotropic transition ($S_C^*$-$S_A$): 84° C.

The following monomers can be prepared in an analogous manner:

4'-(11-Acryloyloxyundecanoxy)-4-biphenylyl 4-[2-amino-5-nitro-4-[(R)-2-octyloxy]phenyl]benzoate,
4'-(11-acryloyloxyundecanoxy)-4-biphenylyl 2-amino-5-nitro-4-[(R)-2-octyloxy]benzoate,
4'-(11-acryloyloxyundecanoxy)-4-biphenylyl 5-amino-2-nitro-4-[(R)-2-octyloxy]benzoate,
p-[trans-5-[10-(2-chloroacryloyloxy)decyl]-m-dioxan-2-yl]phenyl 2-amino-5-nitro-4-[(R)-2-octyloxy]benzoate,
5-(p-undec-10-enyloxyphenyl)-2-pyrazinyl 2-N,N-dimethylamino-4-[(R)-2-fluorohexanoyloxy]-5-nitrobenzoate,
4'-(11-methacryloyloxyundecanoxy)-4-biphenylyl 2-amino-5-nitro-4-[(R)-2-octyloxy]benzoate,
4'-[8-(2-chloroacryloyloxy)octyloxy]-4-biphenylyl 2-amino-6-methyl-4-[(R)-2-fluorohexanoyloxy]-5-nitrobenzoate,
[p-(11-acryloyloxyundecyl)-2-primidinyl]phenyl 2-amino-6-fluoro-4-[(R)-2-fluorohexanoyloxy]-5-nitrobenzoate,
2-amino-4-[(2S,4R,5S)-4-methyl-5-octyl-m-dioxan-2-yl]-5-nitrophenyl trans-4-[p-[8-(2-chloroacryloyloxy)octyloxy]-phenyl]cyclohexyl]methyl ether,
(E)-p-[2-amino-4-[(R)-2-fluorohexanoyloxy]-5-nitrostyryl]phenyl 4-(10-methacryloyloxydecyl)benzoate.

The following polymers can be manufactured in an analogous manner from the aforementioned monomers:

Poly{4'-(11-acryloyloxyundecanoxy)-4-biphenylyl 4-[2-amino-5-nitro-4-[(R)-2-octyloxy]phenyl]benzoate},
poly{4'-(11-acryloyloxyundecanoxy)-4-biphenylyl 2-amino-5-nitro-4-[(R)-2-octyloxy]benzoate},
poly{4'-(11-acryloyloxyundecanoxy)-4-biphenylyl 5-amino-2-nitro-4-[(R)-2-octyloxy]benzoate},
poly{p-[trans-5-[10-(2-chloroacryloyl)oxydecyl]-m-dioxan-2-yl]phenyl 2-amino-5-nitro-4-[(R)-2-octyloxy]benzoate},
poly{methyl[5-(p-undecyloxyphenyl)-2-pyrazinyl 2-N,N-dimethylamino-4-[(R)-2-fluorohexanoyloxy]-5-nitrobenzoate]siloxane},
poly{4-(11-methacryloyloxyundecanoxy)biphenylyl 4-[2-amino-5-nitro-4-[(R)-2-octyloxy]phenyl]benzoate-co-4'-(11-methacryloyloxyundecanoxy)-4-biphenylyl 2-amino-5-nitro-4-[(R)-2-octyloxy]benzoate} (1:1),
poly{4'-[8-(2-chloroacryloyloxy)octyloxy]biphenylyl 2-amino-6-methyl-4-[(R)-2-fluorohexanoyloxy]-5-nitrobenzoate },
poly{[p-(11-acryloyloxyundecyl)-2-primidinyl]phenyl 2-amino-6-fluoro-4-[(R)-2-fluorohexanoyloxy]-5-nitrobenzoate},
poly{2-amino-4-[(2S,4R,5S)-4-methyl-5-octyl-m-dioxan-2-yl]-5-nitrophenyl [trans-4-[p-[8-(2-chloroacryloyloxy)octyloxy]phenyl]cyclohexyl]methyl ether}, poly{(E)-p-[2-amino-4-[(R)-2-fluorohexanoyloxy]-5-nitrostyryl]phenyl 4-(10-methacryloyloxydecyl)benzoate}.

What is claimed is:

1. An optical element for efficient generation of short-wave laser light by frequency conversion by means of a wave-guiding layer, wherein the wave-guiding layer comprises a ferroelectric $\chi^{(2)}$-active monomeric or polymeric liquid crystalline material having a periodic structure which permits a quasi phase matching of a guided laser beam, the period length of the three-dimensional structure being equal to twice the coherence length $l_c = \pi/\Delta\beta$ of the material, whereby $\Delta\beta = \beta_o(2\omega) - 2\beta_o(\omega)$, with $\omega$=angular frequency of the fundamental wave, 0=zero-order mode and $\beta$=propagation constant of the mode.

2. An optical element according to claim 1, wherein the ferroelectric liquid crystalline material can be used for phase matching of the $d_{21}$ component of the nlo tensor.

3. An optical element according to claim 1, wherein the ferroelectric liquid crystalline material contains a mixture of chiral molecules with a nitroaniline derivative incorporated transversely to the longitudinal axis and liquid crystal molecules which form $S_c$ phases.

4. An optical element according to claim 1, wherein the ferroelectric liquid crystal material forms an $S^*_C$ phase or a higher-order ferroelectric phase which can be dipolarly oriented in the electric field.

5. An optical element according to claim 1, wherein the ferroelectric liquid crystalline material forms an $S^*_C$ phase which is homogeneously oriented in bistable manner by boundary forces.

6. An optical element according to claim 4, wherein the dipolar orientation is fixed by cooling below the glass temperature.

7. An optical element according to claim 1, wherein the ferroelectric liquid crystal material comprises a mixture of chiral nlo-active molecules which form $S^*_C$ phases.

8. An optical element according to claim 3, wherein the mixture has the phase sequence 1-Chol-$S_{mA}$-$S^*_C$-glass.

9. An optical element according to claim 7, wherein the mixture has the phase sequence 1-Chol-$S_{mA}$-$S^*_C$-glass.

10. An optical element according to claim 1, wherein the element is operated in the $S^*_C$ phase so that when an electric field is applied, the $\chi^{(2)}$ property becomes operative but disappears when the electric field is switched off.

11. An optical element according to claim 4, wherein the dipolarly oriented axis is at right angles to a waveguide plane of the wave guiding layer.

* * * * *